US011862300B1

(12) United States Patent
Schmidt et al.

(10) Patent No.: US 11,862,300 B1
(45) Date of Patent: Jan. 2, 2024

(54) FORMULATION GRAPH FOR MACHINE LEARNING OF CHEMICAL PRODUCTS

(71) Applicant: Dow Global Technologies LLC, Midland, MI (US)

(72) Inventors: Alix Schmidt, Midland, MI (US); Ian Clark, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 18/114,398

(22) Filed: Feb. 27, 2023

(51) Int. Cl.
*G06N 3/08* (2023.01)
*G16C 20/70* (2019.01)

(52) U.S. Cl.
CPC .................................. *G16C 20/70* (2019.02)

(58) Field of Classification Search
CPC ......... G16C 20/70; G16C 20/30; G06N 3/084
See application file for complete search history.

(56) References Cited

U.S. PATENT DOCUMENTS

| | | | |
|---|---|---|---|
| 10,984,145 B1 | 4/2021 | Hutchinson et al. | |
| 11,404,144 B1* | 8/2022 | Kang | G16C 20/30 |
| 2022/0180201 A1* | 6/2022 | Sarshogh | G06N 3/084 |

OTHER PUBLICATIONS

Li, et al., "A multi-objective fuzzy graph approach for modular formulation considering end-of-life issues"; International Journal of Production Research, vol. 46, Issue 14 (Jun. 12, 2008) (3 pgs; Abstract Only) https://www.tandfonline.com/doi/figure/10.1080/00207540601050376?scroll=top&needAccess=true.

Heid, et al., "Machine Learning of Reaction Properties via Learned Representations of the Condensed Graph of Reaction"; Journal of Chemical Information and Modeling, vol. 62 (Nov. 4, 2021) (10 pgs) https://pubs.acs.org/doi/10.1021/acs.jcim.1c00975.

Fung, et al., "Benchmarking graph neural networks for materials chemistry"; ChemRxiv, Cambridge Open (Jan. 22, 2021) (17 pgs) https://chemrxiv.org/engage/chemrxiv/article-details/60c7546c469df4f006f44f41.

Qin, et al., "Predicting Critical Micelle Concentrations for Surfactants using Graph Convolutional Neural Networks"; ChemRxiv, Cambridge Open (Apr. 9, 2021) (28 pgs) https://chemrxiv.org/engage/chemrxiv/article-details/60c757469abda21a92f8e6b4.

(Continued)

*Primary Examiner* — Lam S Nguyen
(74) *Attorney, Agent, or Firm* — Brooks, Cameron & Huebsch PLLC

(57) ABSTRACT

Chemical formulations for chemical products can be represented by digital formulation graphs for use in machine learning models. The digital formulation graphs can be input to graph-based algorithms such as graph neural networks to produce a feature vector, which is a denser description of the chemical product than the digital formulation graph. The feature vector can be input to a supervised machine learning model to predict one or more attribute values of the chemical product that would be produced by the formulation without actually having to go through the production process. The feature vector can be input to an unsupervised machine learning model trained to compare chemical products based on feature vectors of the chemical products. The unsupervised machine learning model can recommend a substitute chemical product based on the comparison.

26 Claims, 4 Drawing Sheets

(56) References Cited

OTHER PUBLICATIONS

Aldeghi, et al., "A graph representation of molecular ensembles for polymer property prediction"; Department of Chemical Engineering, Massachusetts Institute of Technology (29 pgs) (Accessed: Aug. 26, 2022) chrome-extension://efaidnbmnnnibpcajpcglclefindmkaj/ https://arxiv.org/ftp/arxiv/papers/2205/2205.08619.pdf.

Citrine Informatics—"GEMD Documentation: Graphical Expression of Materials Data" (2 pgs) (Accessed: Aug. 26, 2022) https://citrineinformatics.github.io/gemd-docs/.

* cited by examiner

FORMULATION GRAPH FOR MACHINE LEARNING OF CHEMICAL PRODUCTS

TECHNICAL FIELD

The present disclosure relates to machine learning of chemical products using a formulation graph. Such techniques can be useful to predict an attribute of a chemical product without actually having to make the chemical product. Such techniques can be useful to understand available chemical products and recommend replacement chemical products that can be substituted in downstream applications or downstream formulations.

BACKGROUND

Artificial neural networks (ANNs) are networks that can process information by modeling a network of neurons, such as neurons in a human brain, to process information (e.g., stimuli) that has been sensed in a particular environment. Similar to a human brain, neural networks typically include a multiple neuron topology, which can be referred to as artificial neurons. An ANN operation refers to an operation that processes inputs using artificial neurons to perform a given task. The ANN operation may involve performing various machine learning algorithms to process the inputs. Example tasks that can be processed by performing ANN operations can include machine vision, speech recognition, machine translation, social network filtering, and medical diagnosis, among others.

Machine learning and statistical analysis can be used to assist in designing chemical products. Some empirical modeling methods use training data including independent variables that describe the chemical system of interest. Examples of such variables include descriptors ("X variables") and the desired attributes ("Y variables") of the chemical product to be produced. Various algorithms can detect and encapsulate the patterns between X and Y variables. Model tools can be developed to enable users to test hypotheses about predicted outcomes of a new set of input variables, or optimize inputs to meet a desired Y variable specification for a chemical product.

SUMMARY OF THE DISCLOSURE

The present disclosure is directed to a new way of representing chemical formulations to be used in machine learning models that strive to address existing shortcomings of such models with some previous approaches to representing chemical formulations. For example, the formulation can be represented as a digital formulation graph structure (e.g., a tree) for input to a graph-based algorithm such as a graph neural network (GNN). The digital formulation graph represents or includes the manufacturing history of the ingredients used in the formulation. The "first-level" formulation for the chemical product only includes those immediate ingredients that are mixed together in a final step to manufacture the chemical product. The first-level formulation may also be referred to as the product recipe. However, those ingredients may also be mixtures of other ingredients (e.g., by formulation, blending, chemical reaction, etc.). The digital formulation graph can include representations of each ingredient backwards toward the leaf nodes until a logical conclusion is reached, such as the source monomers or the purchase of a raw material. The use of such a digital formulation graph in machine learning algorithms can enable a more accurate prediction of an attribute of a chemical product produced according to the formulation. Using digital formulation graphs as descriptors can allow for much broader and faster scaling of machine learning capabilities across chemical producer product lines. Instead of each project taking months to collect descriptors, data is nearly instantly available from formulation databases.

As a specific example, the effectiveness of machine learning models using digital formulation graphs of a formulation for a chemical product in predicting an attribute of the chemical product is described herein. The machine learning models can be used to predict one or more attributes of the chemical product resulting from the formulation, without having to actually produce the chemical product, which can be time consuming and/or expensive, particularly when it is desirable to test different formulations. The present disclosure provides improved model performance compared to the use of either a statistical model with formulation data or a statistical model with formulation data and ingredient descriptors. The ingredient descriptors may be difficult, costly, and/or time consuming to obtain.

The machine learning models can be used to compare chemical products based on feature vectors and performance characteristics of the chemical products. The chemical products do not have to be produced, which can save time and/or expense, particularly when it is desirable to test different formulations. The machine learning models can be used to recommend a substitute chemical product for a particular chemical product based on the comparison. For example, a particular chemical product may be temporarily unavailable or too expensive for a desired formulation or application and a substitute chemical product may be desired to replace the particular chemical product without sacrificing performance characteristics provided by the particular chemical product.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Figure 1:
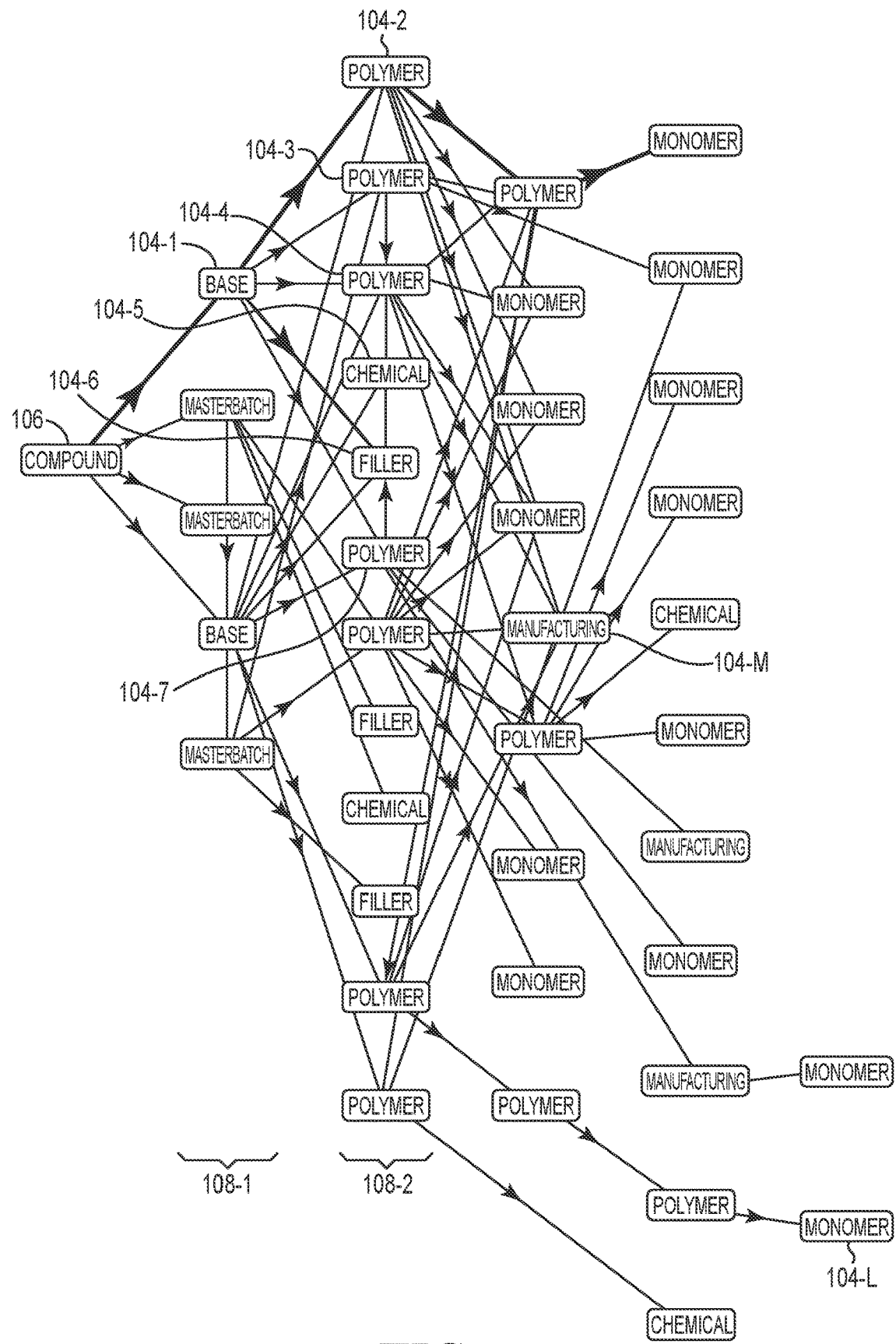
FIG. 1 is an example of a formulation graph for a chemical product.

The development of chemical formulations (blends of chemical ingredients that achieve targeted bulk properties of the entire mixture) is a unique skill. Formulation ingredient choice and preference may be shaped by intuition and/or experience that is neither easily documented nor easily found. In the aggregate, chemical formulations can be described as a matrix where each column is an ingredient that appears in at least one chemical formulation, and each row is a chemical product (e.g., a formulation sample) with the weight fraction of each ingredient presented numerically. The terms weight fraction and weight percent are used interchangeably. There may be hundreds of ingredients used in a training data set, but only tens used within a single formulation. As an example, for every row, there may be 190 zeroes and 10 non-zero values. Additionally, each ingredient is usually used in only a minority of formulations, so every column is also mostly zeroes with a few non-zero values. Thus, the data is highly sparse with variables being highly unbalanced and non-normal. The sparsity of the data makes it difficult to model. However, formulation data can be useful for finding new formulations to solve chemical customer problems.

Chemical descriptors may be referred to herein as "X variables" or "X data". Desired attributes of the chemical product to be produced may be referred to herein as "Y variables" or "Y data". The nature of the X data has a significant impact on which modeling techniques are successful in predicting Y from X. For example, X data consisting of a small number (e.g., less than 100) of normally distributed continuous numerical values with no missing values has a very wide range of appropriate algorithms to choose from with high success rates. This type of data is referred to as dense information content. The less dense the information content of the data, the more likely a given algorithm is to miss critical patterns in the data (underfit) and/or attribute a pattern to a random variation in the model inputs (overfit). Underfit and overfit can each result in a less usable or accurate model. The introduction of categorical variables can cause complications. Some algorithms can handle multilevel categorical variables directly, but most use one-hot encoding or create dummy variables, which can introduce sparsity in the form of large numbers of zeroes in the data set. One-hot encoding uses a group of bits that include a single bit having a value of one, where the remaining bits have a value of zero. These variables are not normally distributed and can be highly unbalanced, posing significant challenges to modeling. Another form of data sparsity can be introduced by missing data. Few algorithms can handle missing data directly. Most algorithms require imputing data or removing missing rows or columns.

Some well-developed use cases of data-driven modeling in chemical design are around small molecule discovery (e.g., using the properties of an individual molecule to predict its performance in some system). "Properties of a molecule" can mean many things, and researchers have investigated representing molecules via their physical properties (e.g., boiling point, measured solubility, etc.), their electronic properties (e.g., density functional theory (DFT) descriptors), and their structures (e.g., simplified molecular-input-line-entry-system (SMILES) or graph representations of the chemical structure). Most of this data tends to be relatively dense continuous variables. In contrast and as described above, formulations have a very different data structure.

To address the highly sparse formulation matrix problem, some previous approaches add more subject-matter expertise into the system in the form of descriptors of the individual ingredients. If descriptors can be acquired for enough of the ingredients, then formulation descriptors can be calculated for the mixture of ingredients. These could be model-based insights or things as simple as weighted average viscosity of a blend of fluids. The table of formulation descriptors can be used to add information density to the data table as well as infusing the model with chemical know-how from subject matter experts, which can result in improved modeling success.

However, efforts to obtain chemical descriptor data to overcome the sparsity of formulation data are expensive and time consuming. Furthermore, first-level formulation data is a sparse matrix that is low in information density and an inappropriate fit for many modeling algorithms. The sparse matrix can be unwieldy and highly susceptible to noise. In some previous examples it may take months to gather sufficient descriptor information for complex formulations. Mining ingredient descriptors from lab notebooks or vendor data sheets and/or experimentally measuring individual ingredient properties are resource intensive. Some such modeling exercises may involve more than 80% of the total time spent gathering descriptor data and less than 20% actually modeling. In many cases, even after the work is as pragmatically complete as possible, the ingredient descriptor set still suffers from significant missing data. Some classes of ingredients may not be well described, while others have little to no data. Depending on the prevalence of certain ingredients, the missing data can propagate through the formulation calculation and produce significant amounts of missing data in the formulation descriptor tables. Modeling is more efficient and accurate when the descriptors are complete enough to capture the performance and loading of the ingredients so that the formulation matrix can be left out of the training data. However, such approaches can produce significant amounts of missing data in the formulation descriptor tables.

Furthermore, inclusion of formulation data may be particularly useful for polymeric ingredients, as their descriptors are often inadequate to capture structure distribution, microstructure detail, and product-by-process information. While a wide range of descriptors can be generated for small molecules, the same is not the case for large molecules such as polymers. Many finished product formulations are blends of polymeric ingredients. Bulk properties of the polymers, such as molecular weight (Mw), polydispersity (PD), or subject matter expertise indicated properties such as percent hydroxide (% OH) may be available, but these may be inadequate for capturing the level of precision that determines the ingredient's performance in the mixture. In these cases, the presence or absence of an ingredient in a formulation is still expressing information beyond its bulk descriptor, so the formulation data is still beneficial.

At least one embodiment described herein addresses the above and other deficiencies by introducing a new way to represent chemical formulations used in machine learning models. The relatively inexpensive formulation data can be used to make predictions of chemical product attributes using digital formulation graphs to overcome sparsity to better train models on sparse data. Describing a chemical product by its formulation graph leverages the availability of formulation data versus ingredient descriptor data. The formulation data is essentially free because the organization performing the formulation would inherently know what ingredients are being used in the formulation. The formulation data in graph form can add significant information density versus the sparse matrix. A graph database can be maintained that includes a list of the ingredients used in any formulation available to a chemical product producer. By including the ingredients in the formulation graph, which is input to the machine learning model, some descriptive information is inherently added by indicating from what ingredients a chemical product is made. The material formulation tree, represented as a digital formulation graph, can be used as a graph structure for input to graph-based algorithms such as GNNs.

An ANN can perform machine learning tasks by forming probability weight associations between an input and an output. The probability weight associations can be provided by a plurality of nodes that comprise the ANN. The nodes together with weights, biases, embeddings, and/or activation functions can be used to generate an output of the ANN based on the input to the ANN. Nodes of the ANN can be grouped to form layers of the ANN. Deep learning is a type of machine learning that has been enabled by improvements in computational power, data availability, and software tools. Deep learning can apply ANNs to accomplish tasks once thought impossible for a computer to perform. The "deep" of deep learning refers to the use of multiple layers in an ANN. These layers extract successively higher order features from a raw input. A GNN is an ANN for processing data that can be represented as a digital formulation graph. GNNs can use pairwise message passing such that graph nodes iteratively update their representations by exchanging information with neighboring nodes that are connected by an edge.

Some previous approaches to using graphs to represent materials do so from the perspective of the finally produced chemical product. In other words, the chemical product is produced (either physically or in silico) and then the chemical structure is modeled as a graph. Some such approaches may represent a single small molecule as a graph. Some such approaches use graphs to represent solid materials such as periodic crystals, surfaces, and/or alloys. Some such approaches use graphs to represent polymer distributions as an example of molecular graphs. Such approaches apply a static representation of the final product, not the composition of a product by its manufacturing history.

Some previous approaches to using graphs and/or trees to describe the ingredients to a product, such as an assembled device (a physical product rather than a chemical product). Some previous approaches describe modeling synthetic routes using a reaction graph. However, the scope of such approaches does not include non-reactive formulated materials nor the utility of the graph as a description of the final product composition rather than the synthetic chemical route to achieve a product.

As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected and, unless stated otherwise, can include a wireless connection.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention and should not be taken in a limiting sense.

FIG. 1 is an example of a formulation graph 100 for a chemical product (e.g., a formulated rubber product). The formulation can include combinations of ingredients to produce the chemical product. Those combinations can include, for example, mixtures, compounds, or other combinations of ingredients formed by chemical reactions, physical reactions, or no reactions (e.g., simple combinations). The ingredients that go into the formulation can include monomers and/or other ingredients such as polymers, bases, masterbatches, fillers, dyes, chemicals, and/or manufacturing ingredients. The chemical product and each ingredient in the chemical formulation can be represented by a respective node (e.g., node 104-1) in the formulation graph 100. A root node 106 represents the chemical product. The remainder of the nodes each represent a respective ingredient of the formulation. The formulation graph 100 includes edges that exist between respective parent nodes and respective child nodes, which indicates that the ingredient represented by the child node was used in whole or in a combination with other ingredients to form the ingredient represented by the parent node. For example, the edge 102 between node 104-1 and node 104-2 indicates that the polymer represented by node 104-2 is an ingredient in the base represented by node 104-1.

The formulation graph 100 has a tree structure with layers. As presented in FIG. 1, successive layers are represented by adjacent columns of nodes. The columns of nodes are not related to columns of a formulation matrix, as discussed further herein. Different columns of the formulation graph 100 are separated by edges between nodes. For example, the edge 102 between node 104-1 and node 104-2 indicates a differentiation between column 108-1 and column 108-2. A given layer (column) includes child nodes that represent ingredients that make up the ingredient(s) or chemical product represented by the parent nodes in the column immediately to the left of the given column. The ingredients in column 108-1 represent a first level formulation, which includes those ingredients that are included in the last combination to form the chemical product.

The formulation graph 100 can be created based on the information available to the chemical product producer. For example, if the chemical product producer uses a manufacturing ingredient in the chemical formulation and the producer does not know the makeup of the manufacturing ingredient, it can be included in the graph without including any of the ingredients (e.g., monomers) that went into producing that manufacturing ingredient. Node 104-M is an example of a manufacturing ingredient for which there is no further chemical ingredient information included in the formulation graph 100. This also makes node 104-M a leaf node of the formulation graph 100. Another example of a leaf node is node 104-L, which represents a monomer.

The formulation graph 100 can be represented structurally from just a list of edges, with each edge being a directional connection between two nodes. For example, the edge 102 forms a directional connection from the node 104-1 to the node 104-2. When stored or presented digitally, the formulation graph 100 may be referred to as a digital formulation graph 100. Each formulation can have its own digital formulation graph, where each graph represents a unique chemical product produced by a different formulation. Collectively, the digital formulation graphs form a data set that describes multiple chemical product formulations.

A list of embedding vectors can be provided for the formulation graph 100, where a respective embedding vector can be provided for each respective node in the formulation graph 100. The list of embedding vectors may also be referred to as an embedding matrix. The respective embedding vector can be made up of numerical continuous data having a length "N". In some embodiments, the embedding vector can include a respective index for each unique ingredient represented by a node in any of the formulation graphs in the data set. In some embodiments, the embedding vector can include a respective index for some but not all of the unique ingredients represented by a node in any of the formulation graphs in the data set (e.g., ingredients that are known or suspected not to contribute to the chemical product attribute can be omitted from the embedding vector). The values in the indices of a particular embedding vector for a particular node can be based on weight fractions of ingredients represented by child nodes that have an edge with the particular node. The indices that correspond to ingredients that are not represented by child nodes that have an edge with the particular node can have a value of zero (0). Because each formulation graph only includes a subset of the total possible unique nodes in the data set, the size of the embedding matrix for each formulation graph is [(number of nodes, N], and the indices of each embedding vector in the embedding matrix map to a node in the formulation graph.

With respect to FIG. 1, the embedding vector for node 104-1 can include an index value corresponding to a weight percent of 50% for the polymer indicated by node 104-2, an index value corresponding to a weight percent of 0.5% for the polymer indicated by node 104-3, an index value corresponding to a weight percent of 1.5% for the polymer indicated by node 104-4, an index value corresponding to a weight percent of 2.2% for the chemical indicated by node 104-5, an index value corresponding to a weight percent of 20% for the filler indicated by node 104-6, and an index value corresponding to a weight percent of 3.1% for the polymer indicated by node 104-7. "An index value corresponding to a weight percent" means that the digital value stored in that index corresponds to the stated weight percent, even if the digital value is a different (e.g., normalized) number. The remaining index values for the embedding vector for node 104-1 can be initialized as zero, a random number, or other values. Some additional index values associated with other nodes are illustrated in FIG. 1 along various edges, but not all index values are illustrated so as not to obscure other details illustrated therein.

In some embodiments, the embedding vector can include additional indices that can be used to add additional information (other data) about each node, such as processing conditions, chemical descriptors of the ingredients, etc. Chemical descriptors can be obtained, for example, by analytical characterization or computational calculations. In such embodiments, the embedding vector can include more than one index for each unique ingredient represented by a node in any formulation graph in the data set, where a first index is based on the weight fractions and a second index is based on the other data.

The formulation graph 100 (e.g., as represented by a list of edges) and the embedding vectors (embedding matrix) associated with the formulation graph 100 can be input to a GNN trained to produce a feature vector for the formulation graph 100 based on the embedding vectors and an architecture of the GNN. The training of the GNN is described in more detail below. The feature vector produced by the GNN is a denser representation of the formulation than the formulation graph 100. The feature vector can be input to a supervised machine learning model trained to predict an attribute value of the chemical product based on the feature vector. The supervised machine learning model can be a classification or regression layer of the GNN itself or a separate machine learning model, such as a linear regression model, a logistic regression model, a partial least squares regression model, a random forest model, a support vector machine model, a regularizing gradient boosting model, etc. The attribute value of the chemical product can be received from the supervised machine learning model without actually having to create the chemical product and measure the attribute value.

The feature vector can be input to an unsupervised machine learning model trained to compare chemical products based on feature vectors and performance characteristics of the chemical products. An unsupervised learning task is one that models the underlying structure of the data without explicit labels (Y data) for each sample. Such methods can identify previously unknown patterns or features in the data. In this example, the unsupervised learning task can provide a recommendation of a substitute chemical product for a particular chemical product. Some examples of methods for unsupervised learning include principal component analysis (PCA), which is a dimension reduction technique that emphasizes data variance, clustering algorithms such as k-means, similarity analysis such as k-nearest neighbor, association rules mining, and anomaly detection.

Figure 2:
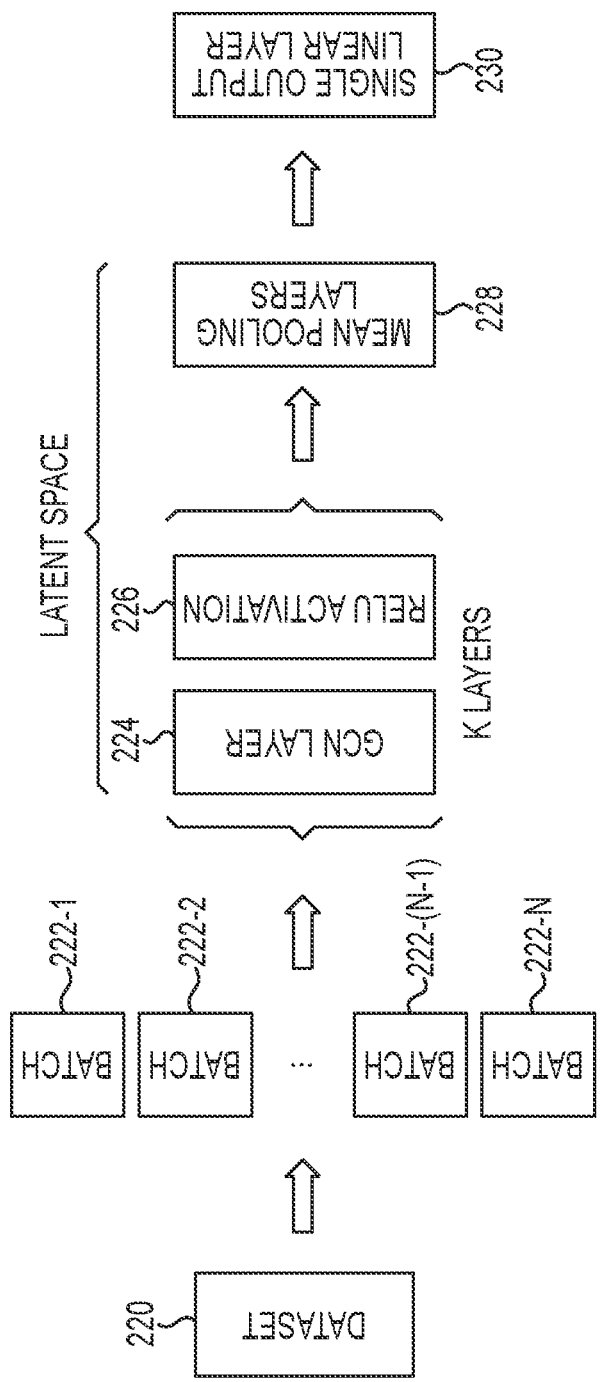
FIG. 2 is a block diagram illustrating an example of training a graph neural network.

FIG. 2 is a block diagram illustrating an example of training a GNN. The GNN can be trained with a training data set 220. The data set 220 can include different digital formulation graphs for different chemical formulations for different chemical products that have already been created. Because the chemical products have already been created, known attribute values of the chemical products are available for training the GNN and/or the machine learning model that predicts the attribute value(s). A respective embedding vector can be provided for each node in each graph as described herein. A respective embedding vector describes a respective node. The embedding vector can have a length at least as long as the quantity of unique nodes (unique ingredients) that appear in any digital formulation graph in the data set 220. The respective embedding vector for a respective node can be initialized with random values, with zero values, or based on other criteria. For example, the embedding vector can be initialized based on weight fractions of ingredients represented by child nodes that have a respective edge with the respective node. A list of embedding vectors (e.g., an embedding matrix) for the nodes in the graph can be provided for each digital formulation graph.

The GNN can be trained with the input of batches 222-1, 222-2, 222-(N−1), 222-N of digital formulation graphs from the data set 220 and can output a respective predicted feature vector and/or attribute for each digital formulation graph (for each chemical product). The GNN can be trained to learn to optimize the embedding vectors for each node and to tune the weights and biases of the neural network to minimize the error of the predictions of the GNN relative to the known true values. The predictions of the GNN can include a feature vector for each digital formulation graph. The predictions of the GNN can include attribute value(s) for those cases in which the GNN itself predicts the attribute value(s) versus another machine learning model. The GNN can use a process known as message passing to distinguish between digital formulation graphs and find a meaningful, vectorized representation of each digital formulation graph, referred to herein as a feature vector. Examples of message passing functions include simple summation, weighted averaging, and graph attention networks, among others.

The embedding vectors can be passed through convolution layers to abstract away the features of the digital formulation graph. Each node's embedding vector can be aggregated across the embedding vectors of neighboring nodes in each digital formulation graph to express the unique characteristics of the digital formulation graph. The aggregation process is part of producing the feature vector by the GNN. The aggregation process can be repeated iteratively (e.g., over a quantity "k" of layers) according to the architecture of the neural network. Each layer "k" of the network architecture can include a convolution layer 224 and an activation function 226. Examples of the convolution layer 224 include a graph convolution network (GCN) and a graph attention network. The convolution layer 224 can employ message passing such that graph nodes iteratively update their representations by exchanging information with neighboring nodes.

In at least one embodiment, the convolution layer 224 can be a GCN and can operate according to:

$$x_i^{(k)} = \sum_{j \in N(i) \cup \{i\}} \frac{1}{\sqrt{deg(i)} \cdot \sqrt{deg(j)}} \cdot \left(W^T \cdot x_j^{(k-1)}\right) + b$$

where $x_i$ is node i (the node embedding vector being updated), $x_j$ is node j (a neighbor of node i), deg is a degree indicating how many neighbors node i has, W is the tunable weights, b is the tunable bias, and k is a layer of the network.

Nodes should not all have the same importance. Therefore, a weighting factor (attention score) can be assigned to each connection between nodes. The connections between nodes can be represented by $a_{ij}$ where i indicates the node being updated and j represents the neighboring node. The embedding vector is represented by h. W is a shared weight matrix. $W_{att}$ is a tunable weight matrix. For example, if node 1 is connected to each of node 2, node 3, and node 4:

$$h_1 = \alpha_{11} W x_1 + \alpha_{12} W x_2 + \alpha_{13} W x_3 + \alpha_{14} W x_4$$

In at least one embodiment, the convolution layer 224 can be a graph attention network convolution layer and can operate according to:

$$\alpha_{ij} = \frac{\exp\left(a^T LeakyReLU(\Theta[x_i \| x_j])\right)}{\sum_{k \in N(i) \cup \{i\}} \exp\left(a^T LeakyReLU(\Theta[x_i \| x_k])\right)}$$

$$LeakyReLU(x) = \begin{cases} x, & \text{if } x \geq 0 \\ slope \times x, & \text{otherwise} \end{cases}$$

where ReLU is a Rectified Linear Unit. Here, the message passing has extra flexibility with the use of attention. Attention allows for unique parts of the graphs to be highlighted, allowing for better identification of important pieces that make predictions easier. Variable a in this case are the tunable attention weights, $\Theta$ is the message passing tunable weights, and x are the embeddings.

In at least one embodiment, the activation function 226 can operate according to:

$$Max(0, x_i)$$

where $x_i$ are the embeddings from the convolution layer.

The output of the k convolution layers can go to a pooling layer 228. The mean pooling layer 228 can generalize the output of the convolution layer 224 and activation function 226. The mean pooling layer 228 can also be referred to as a readout layer, which provides a fixed-length representation of the digital formulation graph. The fixed-length representation is referred to herein as a feature vector and is described in more detail below. An example of the functionality of the pooling layer 228 is a global mean function:

$$r_i = \frac{1}{N_i} \sum_{n=1}^{N_i} x_n$$

where N is the number of rows (nodes in graph i), i is graph I, n is the row number, x is the embeddings (number of nodes×64), and n in the nth row (node) of embeddings.

The message passing function, the size of each layer, the number of layers, and the pooling layer are neural network hyperparameters that can be used to tune the output of the GNN. The output of the pooling layer 228 of the GNN is a vector having a length determined by the pooling layer 228. The output of the pooling layer 228 is a representation of the chemical product that would be produced by the formulation graph input to the GNN. That representation is referred to herein as a feature vector. A respective feature vector is produced for each graph input to the GNN. The length of the feature vector can be less than the length of the embedding vectors, making the feature vector a denser representation of the chemical product than the original embedding matrix.

The feature vector can be used in supervised machine learning of the attribute of the chemical product. One example of the supervised machine learning model can be included in the GNN itself as one or more classification or regression layers at the end of the network structure (e.g., single output linear layer 230). In training, this layer can non-linearly aggregate the collection of feature vectors produced for each digital formulation graph in the data set 220 to make predictions of the attribute values of the chemical products. The layer 230 can be used to model the graph features against the attribute of the chemical product in training to further improve the tuning of the GNN with iterative adjustment of the weights and biases. In other words, during training, the attribute values of the chemical products associated with each graph in the data set 220 are known and so the GNN can be tuned by comparing the output of the layer 230 to those known values.

After training, the single output linear layer 230 can be used as a form of supervised machine learning to predict the attribute value of the chemical product that would be produced by a particular digital formulation graph input to the (already trained) GNN. In the trained model, a single feature vector can be input to the layer 230 to produce a single output, which is the prediction of the attribute value of the chemical product. Alternatively, a feature vector can be input to a different supervised machine learning model to predict the value of the attribute of the chemical product rather than being input to the layer 230. Examples of such supervised machine learning models include linear regression, logistic regression, partial least squares regression, random forest, support vector machines, and regularizing gradient boosting frameworks such as eXtreme Gradient Boosting (XGBoost.).

In some instances, it may be desirable to predict more than one attribute value per digital formulation graph. For example, it may be desirable to predict a value for a chemical product's density and tensile strength. In some embodiments, the GNN can be trained to optimize the feature vector output from the mean pooling layer 228 for a single digital formulation graph such that a machine learning model can produce the multiple attribute values from a single feature vector. In some embodiments, the GNN can be trained to optimize different feature vectors output from the mean pooling layer 228 for the single digital formulation graph (e.g., via multiple runs of the GNN with different weights, biases, etc.), each feature vector being specific to a particular attribute.

The digital formulation graph can be used in transfer learning. After the GNN has been trained using digital formulation graphs to produce feature vectors useful in the prediction of an attribute value, a transfer function can be determined. The transfer function can predict corresponding attribute values for different attributes (or other information that may be useful with respect to the formulation of the chemical product) based on the learning that occurred during training of the GNN and the differences between the original attribute and the different attribute. The transfer function can be used in transfer learning to train a different GNN or retrain the existing GNN to produce different feature vectors for different purposes (e.g., predicting a different attribute). Such transfer learning training can include tuning the embedding vectors and weights and biases of the GNN to predict the different attribute of the chemical product. Subsequent to the transfer learning, a prediction of the different attribute of a chemical product can be received from the GNN based on the input of a digital formulation graph for the chemical product.

A request can be received (e.g., via a user interface) for a substitute chemical product for a particular chemical product that is to be used in a downstream formulation or application. The feature vector can be used in unsupervised machine learning of a substitute chemical product for a particular chemical product. Although not specifically illustrated, in some embodiments, the single output linear layer 230 can represent an unsupervised machine learning model. The unsupervised machine learning model can be used to compare chemical products based on feature vectors and performance characteristics of the chemical products. A feature vector for each chemical product to be compared can be input to the unsupervised machine learning model to produce a recommendation for one of the chemical products to be the substitute chemical product for a particular chemical product. For example, the nearest neighbor product in the feature space could be identified by minimizing the distance between the feature vectors of the target product and substitute product. The feature vectors can be stored in a database in association with the chemical products that the feature vectors represent. In some embodiments, performance characteristics of the chemical products can also be stored in the database. The performance characteristics can have values that indicate a relative quality of the chemical product for a given formulation or application.

In some embodiments, the unsupervised machine learning model can be configured to recommend a substitute chemical product that has a performance characteristic that is minimally different from the value of the performance characteristic of the particular chemical product versus other chemical products in the database. In some embodiments, the unsupervised machine learning model can be configured to recommend a substitute chemical product that has a performance characteristic that is within a predefined difference from a value of the performance characteristic of the particular chemical product.

For example, a target product may be Product A, with Shore A hardness value of 78.1 and elongation of 135.1%. It may be desirable to identify a substitute product with hardness between 75-80 Shore A and elongation 130-150%, but elongation data for different products may not be available. With no further information, a researcher would need to pick from those products having a Shore A hardness between 75-80 (e.g., between 37 different products in one example database) at random or by experience which materials to test for elongation. Such a process may take some time to find a suitable replacement within the predefined performance range, as many products have an elongation over 200% or even 500%. Instead, according to at least one embodiment of the present disclosure, a GNN can be trained on the hardness data and feature vectors for the products can be obtained. A Euclidean distance matrix between the pairs of feature vectors can be generated, and the nearest product can be selected as a substitute product. Upon measurement, this most similar product ("Product Z") is found to have elongation of 140.6% and hardness 77.2. Product Z does not share any ingredients in common with Product A and would not have been considered according to some previous approaches. However, according to one or more embodiments of the present disclosure, the GNN feature vector can identify it as a suitable substitute on the first attempt.

Figure 3:
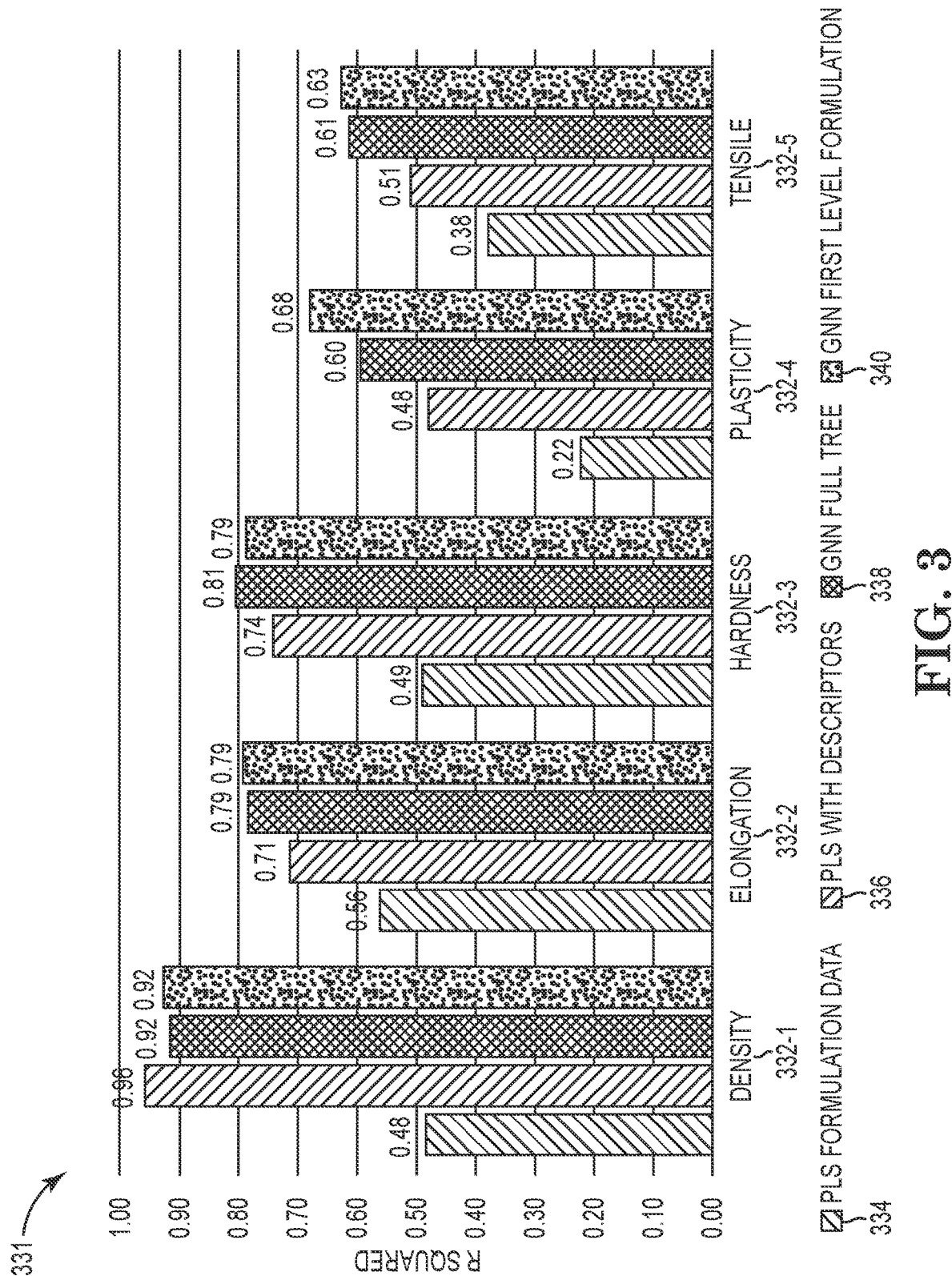
FIG. 3 is a chart illustrating an example of results of chemical product attribute prediction according to various approaches.

FIG. 3 is a chart 331 illustrating an example of results of chemical product attribute prediction according to various approaches. In a specific example, the GNN was trained with a data set including 892 digital formulation graphs for 892 different chemical formulations for different chemical products. Specifically, the chemical products were different rubber materials. The data set included 1667 unique ingredients (nodes) across the 892 formulations. Therefore, the embedding vector for each node was 1×1667 of numerical continuous data. Because each graph includes a subset of the 1667 unique nodes, the starting size of the embedding matrix for each graph is (number of nodes in the graph×1667) and the indices of each embedding vector in the matrix for a given graph map to a node in the edge list. The embedding vectors were initialized with the weight fractions of child ingredients for corresponding nodes. The data set included 41,560 nodes and 65,184 edges. The feature vector output from the pooling layer for each graph had a length of 64.

The GNN was trained to simultaneously learn an improved embedding vector for each node and to tune the weights and biases of the neural network to minimize the mean square error of the predictions relative to the true performance values. The GNN used 7 GATv2Conv layers, with each layer including 64 nodes. The output of each layer was (number of nodes in the graph×64). The layers were linked by a ReLU activation function and output to a global mean pooling layer, as described above with respect to FIG. 2.

Different approaches to predicting the chemical product attribute values were tested and compared to each other. The predicted chemical product attribute values were density 332-1, elongation 332-2, hardness 332-3, plasticity 332-4, and tensile strength 332-5, which are plotted in FIG. 3. The y-axis in FIG. 3 ("R squared") is a statistical measure that represents the accuracy of the prediction (e.g., the quality of the fit of the regression model), where the value 1 is ideal. The results using the first level formulation matrix in a traditional partial least squares (PLS) regression model for each attribute are illustrated at 334. For each attribute, the PLS method on only formulation data produced the weakest results. The results using the addition of descriptors (e.g., expensive X variables, as described herein) with the PLS regression model for each attribute are illustrated at 336. The results using the GNN with the full formulation tree (e.g., as illustrated in FIG. 1), as described herein and according to at least one embodiment, for each attribute are illustrated at 338. The results using the GNN with the first level formulation (e.g., as illustrated by column 108-1 in FIG. 1, instead of the full tree) for each attribute are illustrated at 340.

The addition of descriptors to the PLS method improved the results, but was only superior to the GNN methods in predicting density 332-1. The GNN methods provided superior results for elongation 332-2, hardness 332-3, plasticity 332-4, and tensile strength 332-5, even without the use of descriptors.

Figure 4:
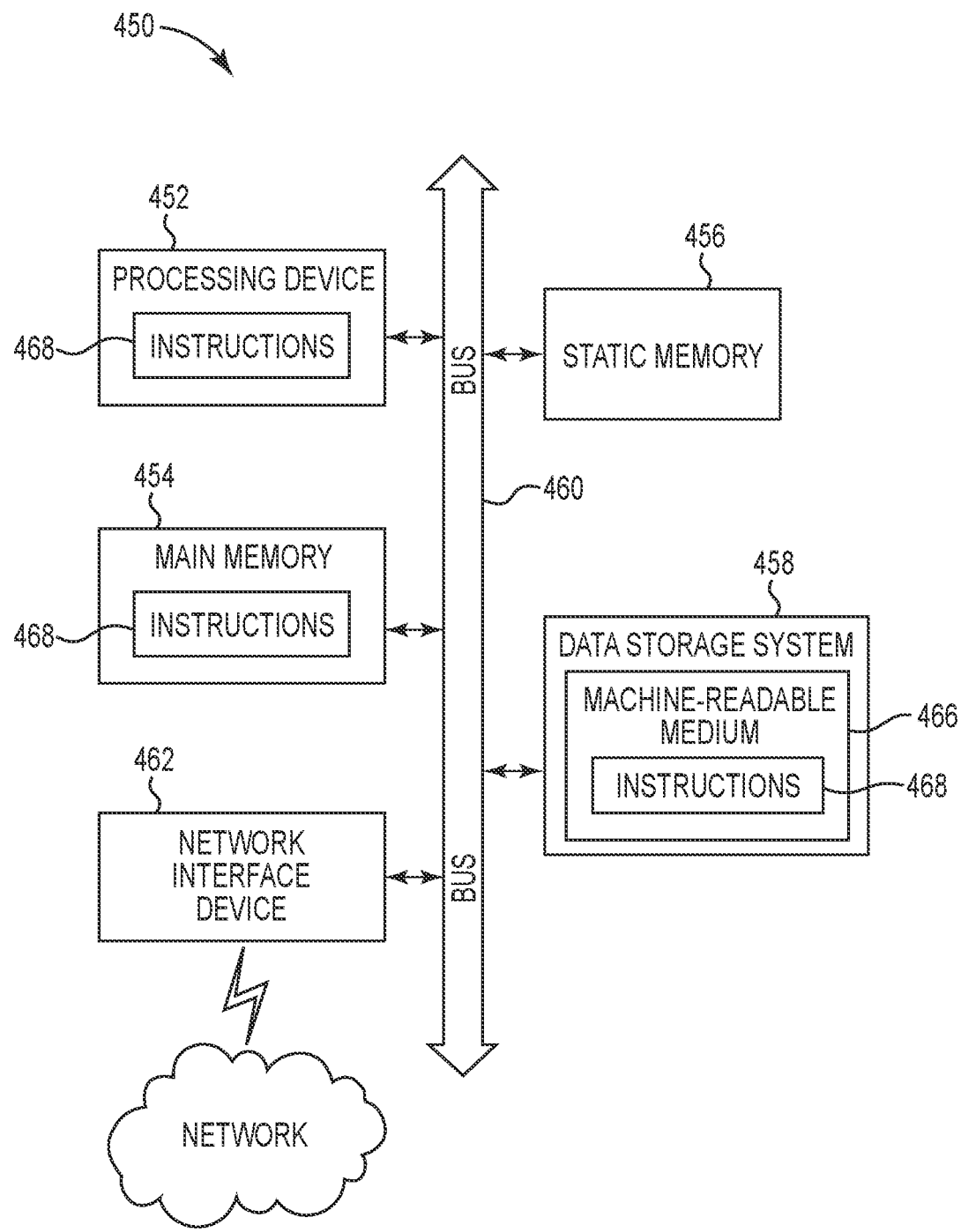
FIG. 4 is an example machine within which a set of instructions, for causing the machine to perform various methodologies discussed herein, can be executed.

FIG. 4 is an example machine 450 within which a set of instructions 468, for causing the machine 450 to perform various methodologies discussed herein, can be executed. The machine 450 can be connected (e.g., networked) to other machines in a LAN, an intranet, an extranet, and/or the Internet. The machine 450 can operate in the capacity of a server or a client machine in client-server network environment, as a peer machine in a peer-to-peer (or distributed) network environment, or as a server or a client machine in a cloud computing infrastructure or environment.

The machine 450 can be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine 450 is illustrated, the term "machine" shall also be taken to include any collection of machines that individually or jointly execute a set (or multiple sets) of instructions to perform any one or more of the methodologies discussed herein.

The example machine 450 includes a processing device 452, a main memory 454 (e.g., read-only memory (ROM), flash memory, dynamic random access memory (DRAM) such as synchronous DRAM (SDRAM) or Rambus DRAM (RDRAM), etc.), a static memory 456 (e.g., flash memory, static random access memory (SRAM), etc.), and a data storage system 458, which communicate with each other via a bus 460.

The processing device 452 represents one or more general-purpose processing devices such as a microprocessor, a central processing unit (CPU), or the like. More particularly, the processing device can be a complex instruction set computing (CISC) microprocessor, reduced instruction set computing (RISC) microprocessor, very long instruction word (VLIW) microprocessor, or a processor implementing other instruction sets, or processors implementing a combination of instruction sets. The processing device 452 can also be one or more special-purpose processing devices such as an application specific integrated circuit (ASIC), a field programmable gate array (FPGA), a digital signal processor (DSP), network processor, or the like. The processing device 452 is configured to execute instructions 468 for performing the operations and steps discussed herein. The machine 450 can further include a network interface device 462 to communicate over the network 464.

The data storage system 458 can include a machine-readable storage medium 466 (also known as a computer-readable medium) on which is stored one or more sets of instructions 468 or software embodying any one or more of the methodologies or functions described herein. The instructions 468 can also reside, completely or at least partially, within the main memory 454 and/or within the processing device 452 during execution thereof by the machine 450, the main memory 454 and the processing device 452 also constituting machine-readable storage media.

In one embodiment, the instructions 468 include instructions to implement functionality corresponding to the GNN and/or unsupervised machine learning model described herein. While the machine-readable storage medium 466 is shown in an example embodiment to be a single medium, the term "machine-readable storage medium" should be taken to include a single medium or multiple media that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media, and magnetic media.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:
1. A method, comprising:
creating a digital formulation graph comprising a plurality of nodes and a plurality of edges based on a formulation for a chemical product, wherein:
a root node represents the chemical product;
a remainder of the plurality of nodes each represent a respective ingredient of the formulation; and
each of the plurality of edges exists between a respective parent node and a respective child node;
providing a respective embedding vector for each respective node;
inputting the digital formulation graph and embedding vectors to a graph neural network (GNN) trained to produce a feature vector for the digital formulation graph based on the embedding vectors and an architecture of the GNN;
inputting the feature vector to a supervised machine learning model trained to predict an attribute value of the chemical product based on the feature vector; and
receiving a prediction of the attribute value of the chemical product from the supervised machine learning model.

2. The method of claim 1, further comprising producing the feature vector by the GNN by passing the respective embedding vector through a plurality of convolution layers, an activation function, and a pooling layer of the GNN.

3. The method of claim 2, wherein producing the feature vector by the GNN comprises aggregating the respective embedding vector of each respective node across the embedding vectors of nodes that have an edge with the respective node.

4. The method of claim 1, further comprising training the GNN with a plurality of digital formulation graphs, each representing a respective formulation for a respective chemical product having a known respective attribute value.

5. The method of claim 4, wherein the respective embedding vector includes a plurality of indices, each index corresponding to a respective unique ingredient represented by a node in any of the plurality of digital formulation graphs; and
wherein the method includes initializing the plurality of indices of the respective embedding vector for each respective node based on weight fractions of ingredients represented by child nodes that have an edge with the respective node.

6. The method of claim 5, wherein the plurality of indices further include a respective first index and a respective second index corresponding to the respective unique ingredient;
wherein the first respective index is based on the weight fractions; and
wherein the second respective index is based on other data associated with the respective unique ingredient.

7. The method of claim 6, wherein the other data comprises processing conditions.

8. The method of claim 6, wherein the other data comprises chemical descriptors of the ingredients.

9. The method of claim 1, wherein inputting the digital formulation graph to the GNN comprises inputting a list of the plurality of edges.

10. The method of claim 1, further comprising receiving a prediction of a plurality of attributes of the chemical product from the supervised machine learning model.

11. The method of claim 10, wherein the plurality of attributes include at least two of a group of attributes comprising density, elongation, tensile strength, and hardness.

12. The method of claim 1, wherein inputting the feature vector to the supervised machine learning model comprises inputting the feature vector to a classification or regression layer of the GNN.

13. The method of claim 12, further comprising training the GNN to predict a different attribute of the chemical product by transfer learning;
tuning the embedding vectors and weights and biases of the GNN to predict the different attribute of the chemical product; and
receiving the prediction of the different attribute of the chemical product from the GNN.

14. The method of claim 1, wherein inputting the feature vector to the supervised machine learning model comprises inputting the feature vector to one of a group of supervised machine learning models comprising:
a linear regression model;
a logistic regression model;
a partial least squares regression model;
a random forest model;
a support vector machine model; and
a regularizing gradient boosting model.

15. A non-transitory machine readable medium storing instructions executable to:
create a digital formulation graph comprising a plurality of nodes and a plurality of edges based on a formulation for a chemical product, wherein:
a root node represents the chemical product;
a remainder of the plurality of nodes each represent a respective ingredient of the formulation; and
each of the plurality of edges exists between a respective parent node and a respective child node;
create a respective embedding vector for each respective node;
operate a trained graph neural network (GNN) on the digital formulation graph and embedding vectors to produce a feature vector for the digital formulation graph based on the embedding vectors and an architecture of the GNN; and
operate a supervised machine learning model to predict an attribute value of the chemical product based on the feature vector.

16. The method of claim 15, wherein the performance characteristic is that of the particular chemical product in a downstream application.

17. A method, comprising:
receiving a request for a substitute chemical product for a particular chemical product, the particular chemical product having a performance characteristic;
creating a digital formulation graph comprising a plurality of nodes and a plurality of edges based on a formulation for the particular chemical product, wherein:
a root node represents the particular chemical product;
a remainder of the plurality of nodes each represent a respective ingredient of the formulation; and
each of the plurality of edges exists between a respective parent node and a respective child node;
providing a respective embedding vector for each respective node;
inputting the digital formulation graph and embedding vectors to a graph neural network (GNN) trained to produce a feature vector for the digital formulation graph based on the embedding vectors and an architecture of the GNN;
inputting the feature vector to an unsupervised machine learning model trained to compare chemical products based on feature vectors of the chemical products; and
receiving a recommendation from the unsupervised machine learning model of one of a plurality of chemical products to be the substitute chemical product.

18. The method of claim 17, further comprising accessing a database that stores a respective feature vector for each of the plurality of chemical products; and
inputting the respective feature vectors to the unsupervised machine learning model.

19. The method of claim 18, wherein a value of the performance characteristic of the substitute chemical product is minimally different from a value of the performance characteristic of the particular chemical product versus the plurality of chemical products in the database.

20. The method of claim 18, wherein a value of the performance characteristic of the substitute chemical product is within a predefined difference from a value of the performance characteristic of the particular chemical product.

21. The method of claim 17, wherein the performance characteristic is that of the particular chemical product in a downstream formulation.

22. The method of claim 17, further comprising producing the feature vector by the GNN by passing the respective embedding vector through a plurality of convolution layers, an activation function, and a pooling layer of the GNN; and
wherein producing the feature vector by the GNN comprises aggregating the respective embedding vector of each respective node across the embedding vectors of nodes that have an edge with the respective node.

23. The method of claim 17, wherein the method includes initializing the respective embedding vector based on weight fractions of ingredients represented by child nodes that have an edge with the respective node.

24. The method of claim 17, wherein inputting the digital formulation graph to the GNN comprises inputting a list of the plurality of edges.

25. The method of claim 17, wherein the unsupervised machine learning model is trained to compare chemical products based on the feature vectors and performance characteristics of the chemical products.

26. A non-transitory machine readable medium storing instructions executable to:
create a digital formulation graph comprising a plurality of nodes and a plurality of edges based on a formulation for the particular chemical product, wherein:
a root node represents the particular chemical product;
a remainder of the plurality of nodes each represent a respective ingredient of the formulation; and
each of the plurality of edges exists between a respective parent node and a respective child node;
create a respective embedding vector for each respective node;
operate a trained graph neural network (GNN) on the digital formulation graph and embedding vectors to produce a feature vector for the digital formulation graph based on the embedding vectors and an architecture of the GNN; and
operate a machine learning model to predict an attribute value of the chemical product or to recommend one of a plurality of chemical products to be a substitute chemical product based on the feature vector.

* * * * *